United States Patent
Conley (10) Patent No.: US 7,905,996 B2
(45) Date of Patent: Mar. 15, 2011

(54) INTERFACE PATCH CLAMPING

(75) Inventor: Edward C. Conley, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 1560 days.

(21) Appl. No.: 10/523,304

(22) PCT Filed: Jul. 28, 2003

(86) PCT No.: PCT/GB03/03179
§ 371 (c)(1),
(2), (4) Date: Aug. 4, 2005

(87) PCT Pub. No.: WO2004/011937
PCT Pub. Date: Feb. 5, 2004

(65) Prior Publication Data
US 2006/0163062 A1 Jul. 27, 2006

(30) Foreign Application Priority Data
Jul. 30, 2002 (GB) .................. 0217564.4

(51) Int. Cl.
*G01N 27/30* (2006.01)
*G01N 33/487* (2006.01)
(52) U.S. Cl. ............. 204/403.01; 204/450; 422/50; 422/82.01; 422/82.02; 435/285.2; 435/285.3; 435/287.1; 435/817
(58) Field of Classification Search .......... 204/433, 204/403.01, 409–418, 450; 600/361, 393, 600/395, 396; 435/173.4–173.8, 431, 470, 461, 287.1, 817, 7.2, 7.21, 173–174, 285.2, 285.3; 422/82.01, 82.02, 50; 205/789, 789.5
See application file for complete search history.

(56) References Cited

U.S. PATENT DOCUMENTS

| | | | | |
|---|---|---|---|---|
| 4,128,456 A * | 12/1978 | Lee et al. | .................. | 435/287.1 |
| 4,671,288 A * | 6/1987 | Gough | .................. | 600/347 |
| 4,960,133 A * | 10/1990 | Hewson | .................. | 607/124 |
| 5,824,061 A * | 10/1998 | Quijano et al. | .................. | 623/1.13 |
| 6,096,000 A * | 8/2000 | Tachibana et al. | .................. | 604/20 |
| 6,135,990 A * | 10/2000 | Heller et al. | .................. | 604/500 |
| 7,101,472 B2 * | 9/2006 | Dineen et al. | .................. | 205/792 |
| 7,270,730 B2 * | 9/2007 | Schroeder et al. | .................. | 204/403.01 |
| 2001/0046706 A1 * | 11/2001 | Rubinsky et al. | .................. | 435/461 |
| 2002/0182627 A1 * | 12/2002 | Wang et al. | .................. | 435/6 |
| 2003/0113833 A1 * | 6/2003 | Oka et al. | .................. | 435/29 |
| 2004/0005696 A1 * | 1/2004 | Vestergaard et al. | .................. | 435/287.1 |
| 2004/0127776 A1 * | 7/2004 | Walker et al. | .................. | 600/310 |

FOREIGN PATENT DOCUMENTS

| | | | |
|---|---|---|---|
| JP | 11-299496 | * | 4/1998 |
| WO | WO 01/71349 | * | 9/2001 |
| WO | WO 02/055653 | * | 7/2002 |

OTHER PUBLICATIONS

Patent Abstracts of Japan, vol. 2000, No. 2, Feb. 29, 2000.

* cited by examiner

*Primary Examiner* — Alexa D Neckel
*Assistant Examiner* — Jennifer Dieterle
(74) *Attorney, Agent, or Firm* — Yonggang Ji (57) ABSTRACT

The present invention relate to methods and devices for holding a cell and positioning recording electrodes inside it.

17 Claims, 5 Drawing Sheets

INTERFACE PATCH CLAMPING

CROSS REFERENCE TO RELATED APPLICATIONS

This application is a filing under 35 U.S.C. §371 and claims priority to international patent application number PCT/GB2003/003179 filed Jul. 28, 2003, published on Feb. 5, 2004 as WO 2004/011937 and also claims priority to patent application number 0217564.4 filed in Great Britain on Jul. 30, 2002; the disclosures of which are incorporated herein by reference in their entireties.

FIELD OF THE INVENTION

The present invention relates to devices of the type mentioned in the preambles of the independent claims for holding living cells for recording purposes.

PRIOR ART

Studies of the electrophysiology of cells involve measuring the flow of ionic current across the cell membrane inducing, or in response to, trans membrane conductance changes. One method of performing this involves holding a cell, penetrating the cell membrane with 1 or 2 microelectrodes and measuring the electrical signals detected by the microelectrode(s). A problem with such studies is that the cell-penetrating needles have been difficult to make and handle and that it has been difficult to hold the cell without harming it while inserting the electrode. Japanese patent application 11-299496 describes a method for inserting a microelectrode into an oocyte in which an oocyte is positioned in or on a container which is provided with microelectrode guiding means. The microelectrode guiding means can be an elongated though hole which has a first end with a diameter greater than the diameter of the needle and an oocyte and a second end with a diameter which is less than the diameter of the microelectrode and an oocyte. The oocyte is positioned in the through hole and then the microelectrode is introduced into the first end of the though hole and lowered until it penetrates the oocyte. In order to prevent breakage of the tip of the microelectrode, an microelectrode holder is proposed. This holder has a central bore into which a microelectrode can be loaded and is provided with an end face provided with protuberances which co-operates with corresponding depressions in the face of the container surrounding the through hole in the container to align the central bore with the through hole. In use a microelectrode is partly introduced into the microelectrode holder, so that its fragile tip does not protrude from the microelectrode holder. An oocyte is placed in the container and then the microelectrode holder is fitted to container with the bore of the microelectrode holder aligned with the through hole of the container. The microelectrode can then be pushed into the container and penetrate the oocyte while being guided by the walls of the container.

A problem with such a system is that it is time consuming as the oocyte has to be first captured, then placed in a container and then penetrated.

SUMMARY OF THE INVENTION

The proposed device in accordance with the present invention comprises a penetrative, optionally, non-return, intracellular electrical access electrode assembly, optionally doped with a sealing compound to prevent ionic leakage. It improves over existing electrode designs in the public domain in that it permits electrode entry for multiple recording at points both inside and outside of cells. It is able to be used such that cells can be manipulated in arrays and brought into contact with electrodes in a controlled manner prior to an automatic gaining of intracellular access. The device is able to be fitted to industry-standard robots to enable large-scale drug profiling applications.

The advantages of this device are in the coupling of the initial cell holding step to the cell penetration step that gives full transmembranal electrical access. This may be achieved by making the cell membrane 'bow' inwards towards the electrodes only under seal conditions and this allows cell penetration by recessed electrode(s): Embodiments of the present invention may have multipoint conductor electrodes, penetrating barbs, independent electrodes and/or doped local lipolysis for access. The use of a lipolytic agent, for example a needle or contact patch made of, or coated with, a conducting lipolytic polymer, is particularly useful to aid electrical access. Optionally, a non-ionically conducting sealing compound to prevent ionic leakage may be used.

The use of penetrative electrodes on cells has been hampered by difficulties in holding individual cells in place prior to electrode insertion. The proposed device(s) get around this with the use of arrayable sheaths, which suck individual cells onto the aperture at the end of each sheath. The proximity event sensing/hold feature enables robust cell seeding and solution dipping methods to be used in different orientations (e.g. vertically with electrodes above the cell, vertically with the electrodes below the cell, inclined, etc.) and different experimental conditions.

According to the present invention, at least some of the problems with the prior art are solved by means of a device having the features present in the characterising part of claim 1 and methods in accordance with claims 7 and 8.

DETAILED DESCRIPTION OF EMBODIMENTS ILLUSTRATING THE INVENTION

An electrode assembly in accordance with the present invention comprises a narrow bore sheath, preferably made of a bio-inert/biocompatible material, preferably mouldable and machinable, such as a combination of rigid plastics, or the like, which are selected due to their insulating and low capacitance properties. The sheath is intended to protect one or more electrode needles mounted inside it and also to provide a tip against which a cell can be captured. Thus, inside the narrow bore there is at least one cell membrane-penetrating electrode needle (with two or more conducting portions electrically insulated from each other and the needle body) which can act as a multi-point access electrode, or there are two or more cell membrane-penetrating electrode needles each of which have at least one conducting portion which can be used as an electrode or there are combinations of single-electrode needles and multi-electrode needles. The conducting portions can be variably connected to electrical supplies or recording preamplifiers according to specific applications. Insulating elements or gaps between the conducing elements prevent short circuits between the conducting elements. Signals can also be sent down to, and/or received from, the cell via the sheath if it is itself conducting or if it is provided with one or more electrodes. Preferably, any change in conductance measured between electrodes near or at the sheath tip, due to the presence of a cell near to the tip, can be sensed and then be used to initiate a small vacuum being applied through the sheath (using microprocessor-controlled syringes or other such suction devices), thus sucking the cell onto the tip of the sheath. Part of the cell may be sucked into the sheath by the suction and penetrated by the needle. The needle and/or the suction may then hold the cell in place, which allows the cell and sensor assembly to be subsequently manipulated. The diameter and wall thickness of the sheath are chosen in order to prevent the cell being sucked completely into the sheath or alternatively, if the inner diameter of the sheath is greater than the diameter of the cell being captured, the interior of the sheath is provided with means to prevent the cell being sucked too far into the sheath. Such means could be, for example, a flange projecting sufficiently far from the inner wall towards the centre of the sheath to prevent passage of the cell, and being provided with electrode needle or needles projecting out of it sufficiently far towards the open end of the sheath so as to ensure adequate penetration of a cell. The cell penetration needle is optionally coated with a non-conducting sealing compound (such as petroleum jelly) which prevents ionic leakage from the cell. A voltage can be applied to some or all of the electrodes from an external stimulator and events may be recorded from some or all of the electrodes. Different electrodes connections can permit signal amplification for sensing voltage, current, metabolites, second messengers and/or provide reference signals to and/or from the cell and/or (if electrodes are placed suitably) from its surroundings.

Figure 1:
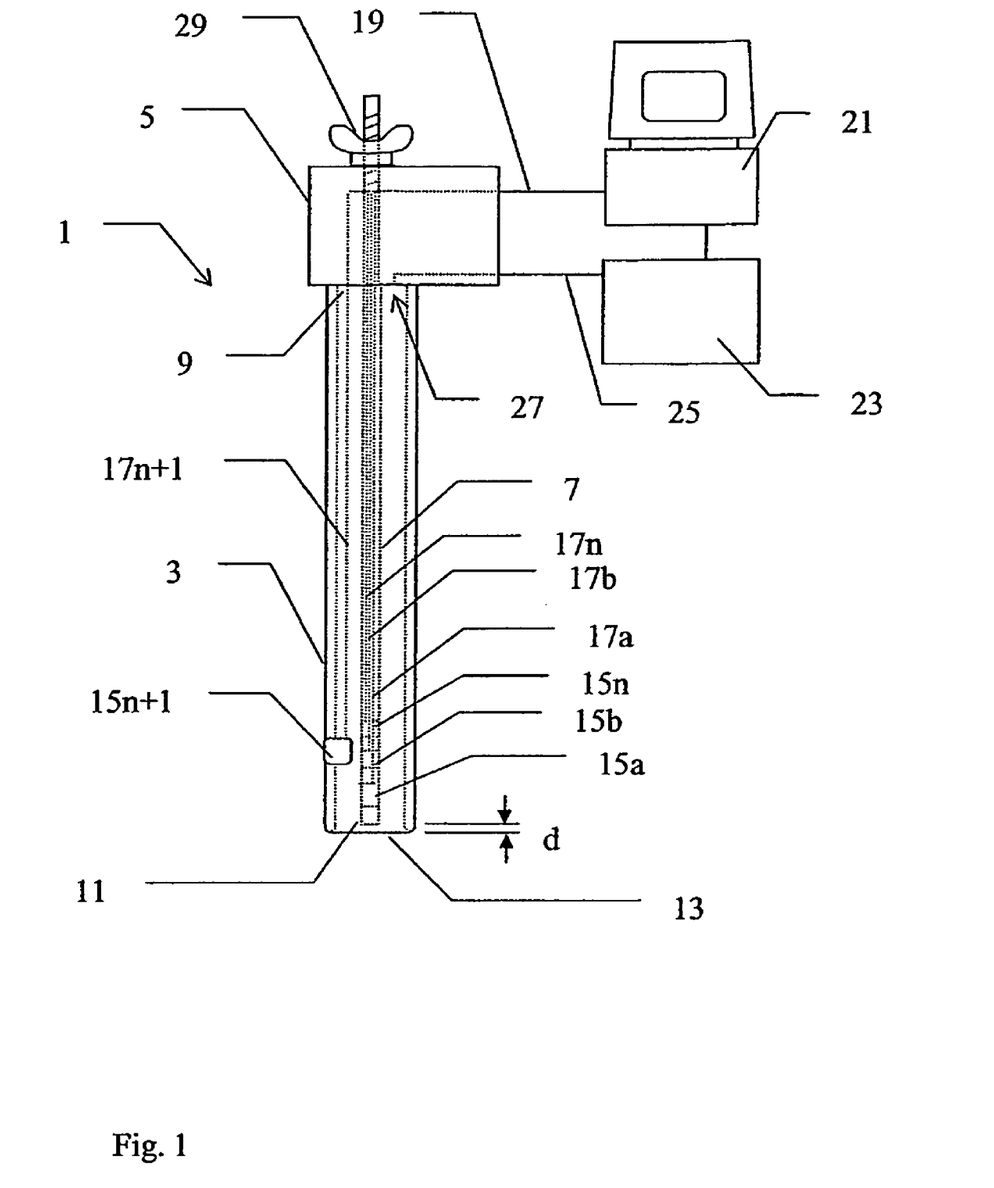
FIG. 1 shows schematically a first embodiment of an intracellular electrical access electrode in accordance with the present invention.

FIG. 1 shows schematically, and not to scale, a first embodiment of an intracellular electrical access electrode assembly 1 according to the present invention. Electrode assembly 1 comprises a hollow, elongated, tubular electrode sheath 3 which projects out of an electrode assembly body 5. Electrode assembly body 5 is intended to be gripped by an operator or mounted on, or gripped by, a robot or to be attached to a movable carriage (not shown) in an automated analysis instrument and it can have any suitable shape. Preferably it is provided with docking features (not shown) such as specially shaped or positioned holes or projections which enable it to be accurately mounted on an automated manipulating device such as a robot arm or carriage or the like. An elongated electrode needle 7 is concentrically mounted inside electrode sheath 3. One end 9 of electrode needle 7 in held in electrode body 5 and the other, free, end 11 of electrode needle 7 is positioned either level with the open tip 13 of electrode sheath 3 or, as shown in FIG. 1, inside the sheath 3 at a small distance d from the open, cell-contact end 13 of the sheath 3. Electrode needle 7 is provided with a plurality of sensing electrodes 15a, 15b, . . . 15n positioned near its free end 11. In this embodiment sensing electrodes 15a, 15b, . . . 15n are in the form of ring electrodes, preferably mounted flush with the surface of electrode needle 7 with the longitudinal axes of the ring electrodes concentric with the longitudinal axis of the electrode needle 7. A further electrode 15(n+1) is provided on the exterior wall of electrode sheath 3. The electrode needle 7 and electrode sheath 3 may be made of insulating material and/or insulating material may be arranged on or in the electrode needle and electrode sheath in order to isolate the electrodes from each other. Electrode needle 7 can be provided with adjustable mounting means 29 (shown schematically) for displacing electrode needle 7 up or down in its longitudinal direction. Adjustable mounting means may be used to move the free end of electrode needle 7 closer to or further away from the open end of electrode sheath 3 in order to vary the depth of penetration of the electrode needle into the cell that it is attached to. Alternatively, electrode needle 7 may be immovably mounted with its tip at a position chosen to ensure penetration of the cell being tested.

Other shapes of electrode are also possible as described below.

Each electrode 15a, 15b, . . . 15n+1 is connected by a conductor 17a, 17b, . . . 17n+1 to an input/output bus 19 of a computing and control device such as a personal computer 21.

Computing and controlling device 21 is programmed to collect signals from electrodes 15a, 15b and to control a source of suction 23, such as a vacuum or suction pump or vacuum tank, connected via a suction line 25 to an opening 27 in electrode assembly body 5 which leads to the interior of electrode sheath 3. The source of suction 23 can be controlled to generate suction in electrode sheath 3.

Figure 2:
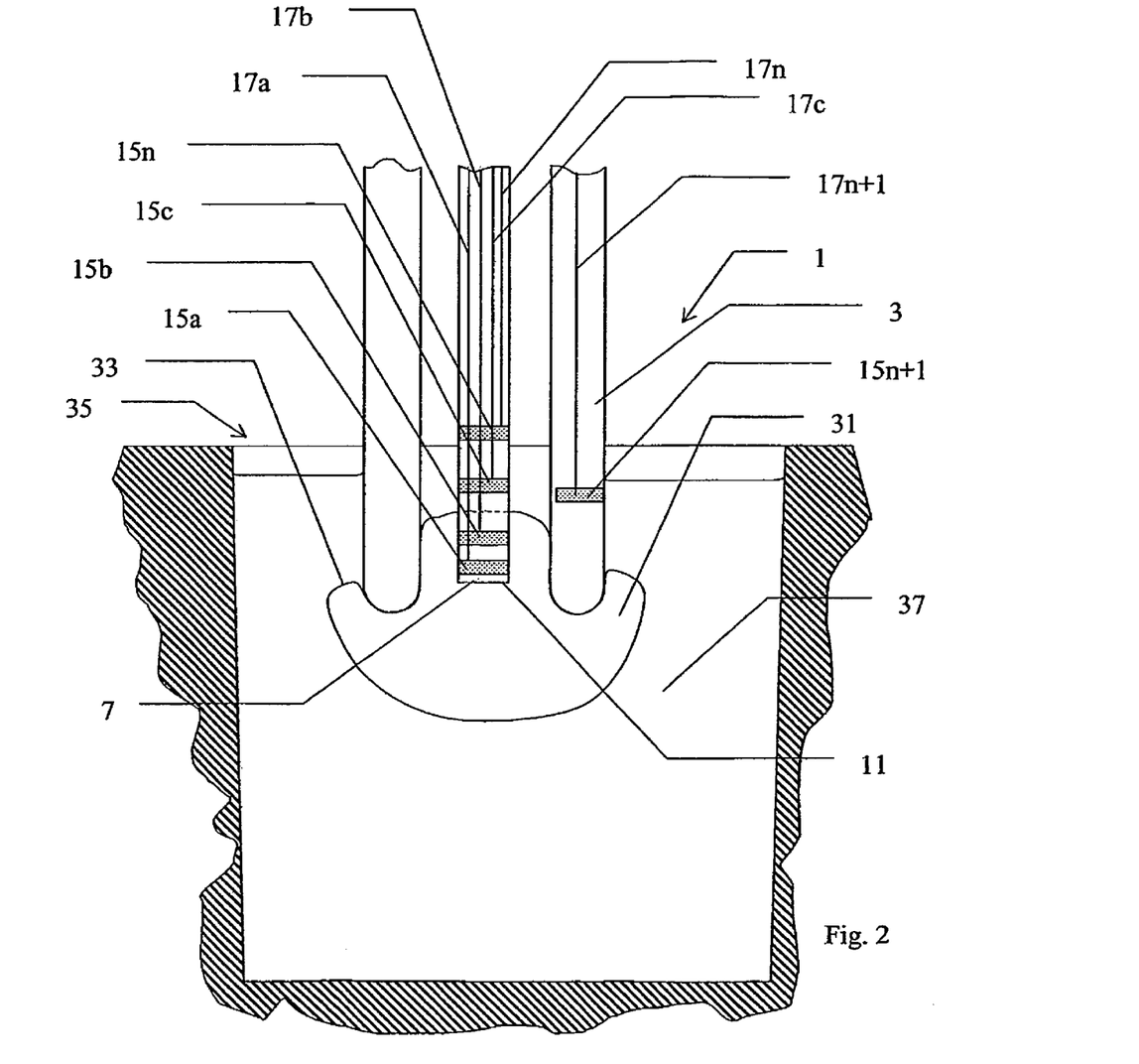
FIG. 2 shows schematically a magnified view of the free end of the first embodiment of an electrode assembly in accordance with the present invention.

FIG. 2 shows an enlarged, schematic, part view of the free end of a first embodiment of an electrode assembly 1 in accordance with the present invention, with a cell 31 positioned on it.

In this example, the cell is an oocyte cell with a diameter of approximately 1 mm. Such a cell can be captured on an electrode assembly in the following manner: the electrode assembly 1 is lowered into a bath containing a plurality of cells; as a cell passes in proximity to the open end of electrode sheath 3, it causes a change in the conductance measured between electrode 15a and electrode 15n+1, and this change of conductance triggers computing and controlling device to operate the source of suction 23 such that a small vacuum occurs within electrode sheath 3, thereby sucking cell 31 onto the open, cell-contact end of the sheath. The bore of the sheath is selected such that the cell 31 is too big to be sucked into the sheath but will be held on the end of the sheath by the negative pressure caused by the application of the vacuum. Suitable sheath bore diameters for 1 mm nominal diameter oocytes are in the range of 0.1-0.8 mm, preferably 0.3-0.6 mm. The dimension is chosen so that the vacuum pulls sufficient cellular material into the sheath to permit electrode needle 7 to penetrate the cell membrane 33, and is therefore also dependent on how far the electrode needle 7 is from the sheath tip 13. Thus, the further the electrode needle 7 is from the sheath tip 13 then the greater the suction force and/or the width of the bore required to enable the cell 31 to be deformed enough to be penetrated. The shank of the electrode needle 7 can be of any suitable width e.g. a width up to 0.1 cell diameters and preferably electrode needle 7 tapers to a sharp narrow point. The width of the needle depends on the stiffness and brittleness of the material that it is made from, as well as the ease of forming the electrode and insulating regions on it. Glass electrodes may have a minimum width in the range of 0.01 mm-10 microns while less rigid materials such as plastics would usually require larger minimum widths. The maximum width of a needle depends on the size of the cell being investigated and in general should not exceed 0.2 of a cell diameter in order to prevent the cell being killed by the needle penetration.

The penetration of the cell results in some electrodes, e.g. 15a, 15b being within the cell, and the remaining electrodes e.g. 15c, 15d, . . . 15n+1 being outside the cell. The penetration of the electrodes is preferably adapted so that only some, e.g. two 15a, 15b, of the electrodes are inside the cell. The electrodes could be spaced at intervals corresponding to 0.1 of the diameter of the cell being investigated, e.g. at 0.1 mm intervals for electrodes intended to enter 1 mm diameter oocyte cells. In this way, when putting two electrodes inside the cell, the penetration of the cell is limited to less than half the cell diameter and the risk of accidently piercing the nucleus of the cell is reduced. If injection into the nucleus is intended than a longer needle may be used. The cell 31 may be positioned in a well 35 on an array containing a plurality of wells and the well 35 may contain a liquid 37 which prevents the cell from drying out. The liquid 37 can be dosed with chemicals and the response of the cell to the chemicals recorded via some or all of the electrodes 15a-15n+1.

Figure 3:
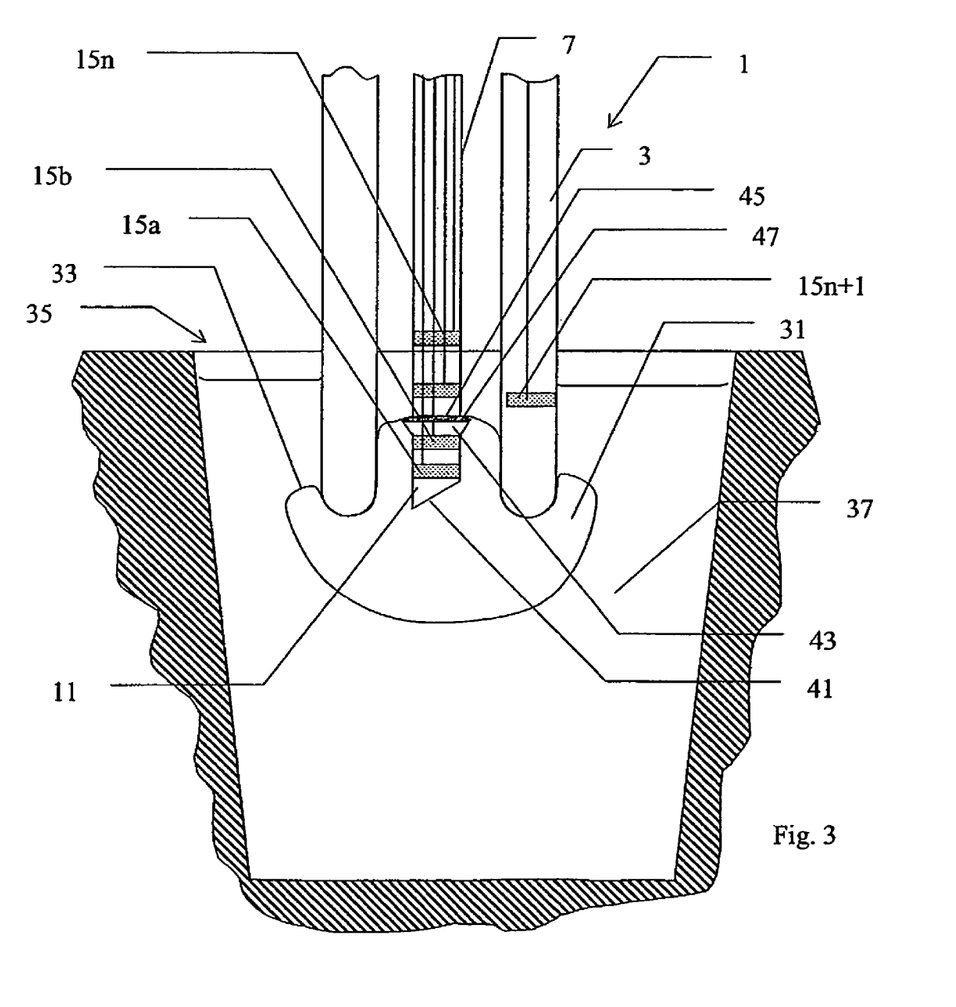
FIG. 3 shows schematically a magnified view of the free end of a second embodiment of an electrode assembly in accordance with the present invention.

FIG. 3 shows an enlarged, schematic, part view of an electrode assembly in accordance with a second embodiment of the present invention in which the same reference numerals are used for features that it has in common with the first embodiment. In this embodiment the electrode needle 7 is provided with a sharp tip 41 at its free end 11. This facilitates passage though the cell membrane. Since the cell membrane is an ionic insulator, physical penetration may cause non-specific ionic leakage which is minimised by the sharp tip 41. An optional cell-removal preventing device such as a barb device in the form of a tapered ring 43 which tapers down towards the needle tip 41 may also be provided in order to resistant accidental removal of the electrode needle 7 from the cell 31, and leakage may be further minimised by applying non-ion-conducting sealing compound 45 (e.g. petroleum jelly) to the ring surface 47 which is intended to face the cell membrane 33 after the electrode needle 7 has been inserted in the cell, and/or to the surface of the needle which is intended to be in the region of the cell membrane during use.

Figure 4:
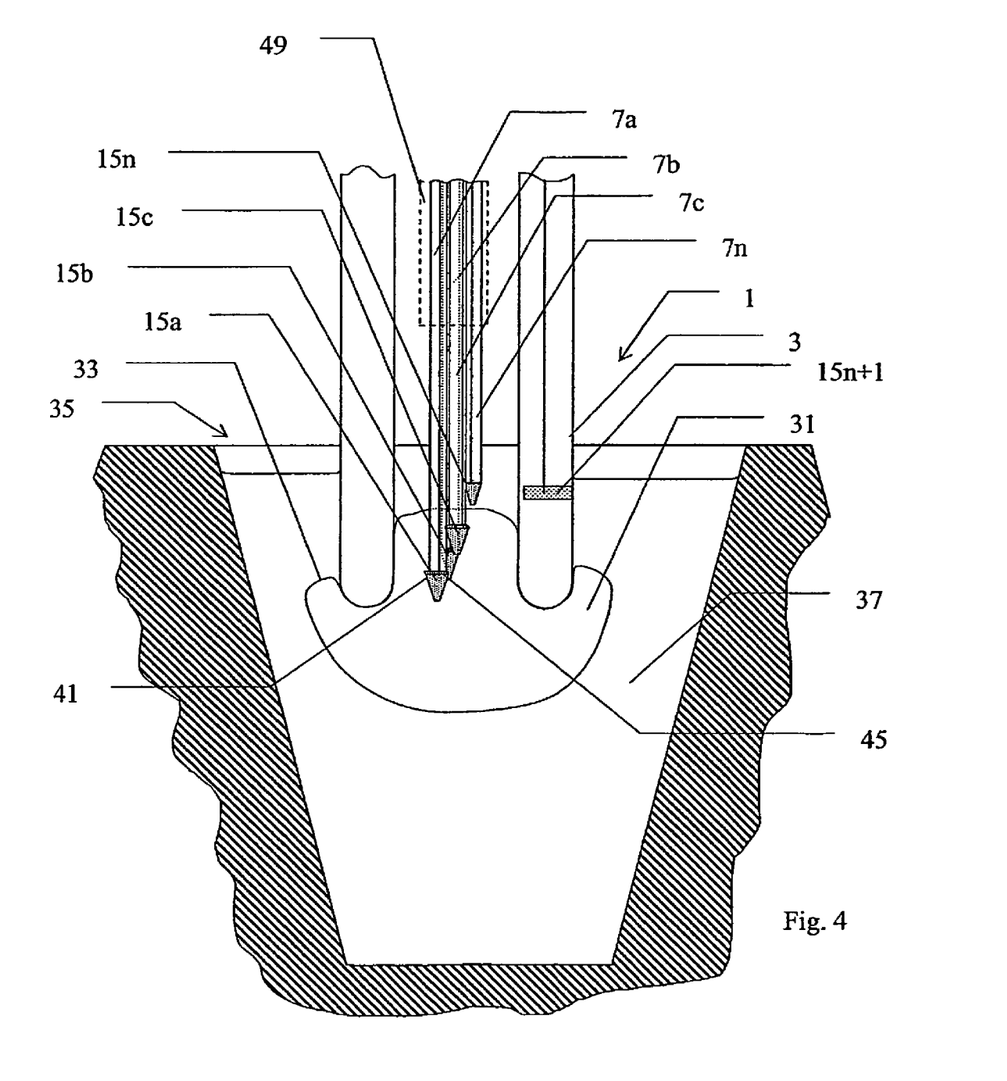
FIG. 4 shows schematically a magnified view of the free end of a third embodiment of an electrode assembly in accordance with the present invention; and, FIG. 5 shows schematically a magnified view of a fourth embodiment of an electrode assembly in accordance with the present invention.

A schematic part view of a third embodiment of an electrode assembly in accordance with the present invention is shown in FIG. 4. This electrode assembly comprises a plurality of electrode needles 7a-7n arranged inside the electrode sheath 3. Each electrode needle 7a-7n is provided with its own tip electrode 15a-15n. Optionally each electrode needle may be provided with a further ring or spot electrode (not shown). Additionally, the individual electrode needles 7a-7n may optionally be joined together, or optionally surrounded by a strengthening tube 49 (shown by dashed lines), along at least a part of their lengths in order to strengthen them and prevent buckling of the individual electrode needles 7a-7n. Each electrode needle may be provided with an individual barb and/or surface provided with non-ion-conducting sealing compound or, as shown in FIG. 4, only the electrode needles 7a, 7b, intended to penetrate the cell membrane, are each provided with a barb 43 and sealing compound 45.

In use the electrode sheath is lowered over a container of cells. When a cell passes sufficiently close to the open end of the sheath such that the conductivity measured between the electrode needle tip electrode and the electrode on the electrode sheath varies, suction is applied to the electrode sheath and the cell sucked up against the end of the sheath. The electrode needle may then be either lowered such that it penetrates ('stings') the cell, or the portion of the cell inside the sheath may be sucked up the sheath by increased suction until the cell membrane is pierced by the electrode needle inside the sheath. The degree of penetration can be made adjustable by providing a means for varying the lowering of the electrode needle or for varying the suction pressure, for example, in order to avoid unwanted penetration of the cell nucleus.

Figure 5:
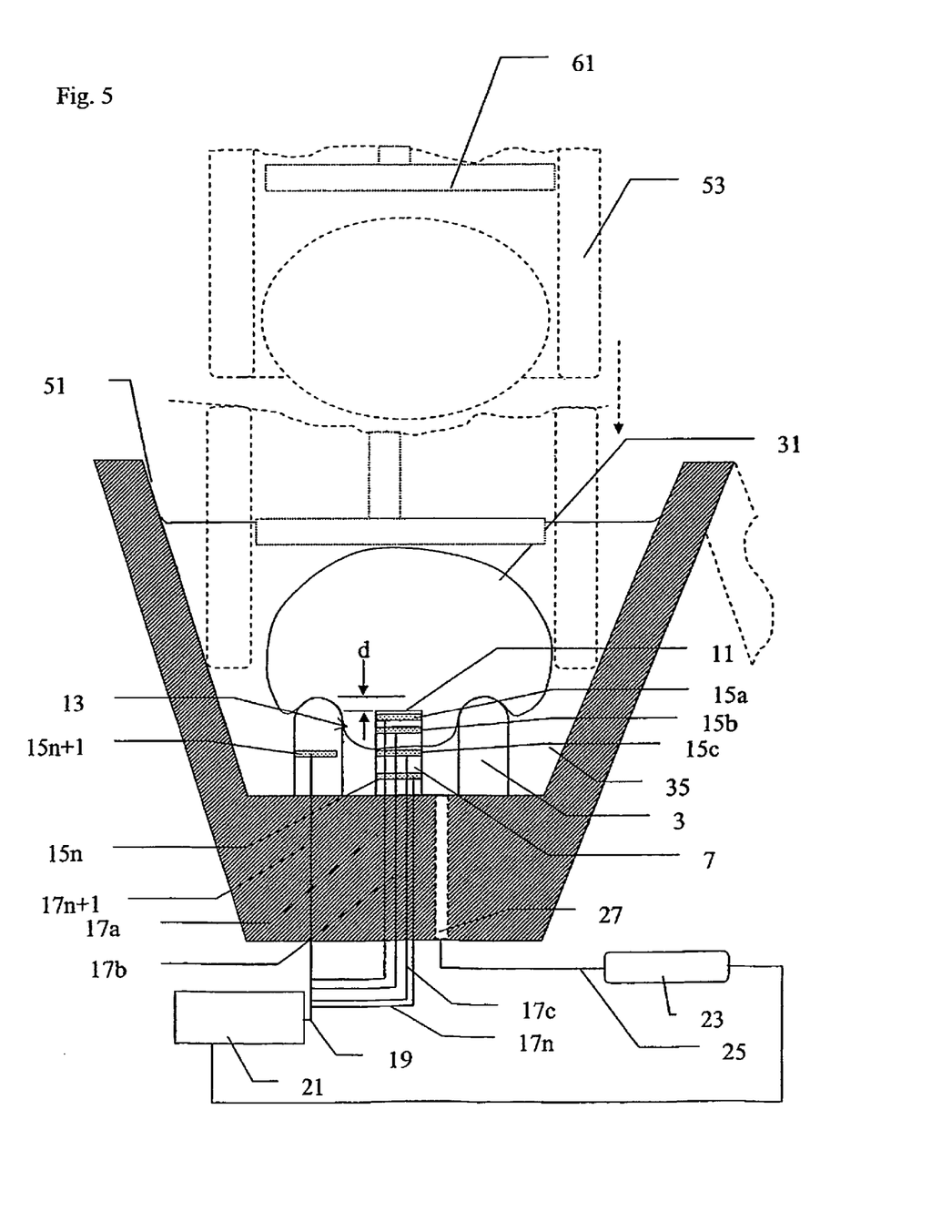

FIG. 5 shows schematically a further embodiment of the present invention. In this embodiment an intracellular electrical access electrode assembly 1 is provided in the base of a well 35. Well 33 may be one well of a number of wells, e.g. 96 well, 384 wells, etc. arranged in rows and columns or circles or spirals, or any other shape on a platter or other supporting substrate.

Intracellular electrical access electrode assembly 1 comprises a hollow tubular electrode sheath 3 which projects up into the well from the bottom of the well 35. Electrode sheath 3 is positioned in the centre of well 35 and the inner walls 51 of well 35 may be straight as shown which allows adequate space around the cell for drug administration, or they may slope inwards towards the bottom of the well to act as aligning surfaces for a cell-positioning device 53. Cell-positioning device (shown in dashed lines) 53 can be any suitable device such a manually or automatically operated pipette containing one or more cells, or a hopper containing one or more cells or the like. As cell-positioning device 53 is lowered, the end of it comes into contact with well wall 51 which guides it to a central position above electrode sheath 3. Once it has been lowered as far as it can go, cell 31 can be ejected from it by a plunger 61 onto the open end of electrode sheath 3. An elongated electrode needle 7 is concentrically mounted inside electrode sheath 3. The dimensions of the sheath and needle are adapted to the average diameter of the cell being examined. The sheath should have a diameter small enough to prevent the cell being pulled into the sheath while at the same time the sheath should a diameter which is sufficiently large such that the contact area between the sheath and cell is large enough to prevent damage to the cell. Preferably sheath 3 has a diameter between 0.2 and 0.8 of the average cell diameter. Electrode needle must be long enough to accommodate all the electrodes necessary for the experiment being carried out on the cell, while also being rigid enough to avoid being damage when penetrating the cell and when being manufactured and positioned in the well. Preferably electrode needle 7 is at least 1 cell diameter long and up to 0.1 cell diameters wide. One end 9 of electrode needle 7 is fixed to the well bottom and the other free end 11 of electrode needle 7 is positioned either level with the open end 13 of electrode sheath 3 or, as shown in FIG. 5, inside the sheath 3 at a small distance d from the open, cell-contact end 13 of the sheath 3, in order to allow sheath 3 to protect it from damage. Distance d can be adapted to the size of the cell being penetrated and, in order to prevent the cell from being deformed too much when bringing it into contact with the needle 7, it should not be too large. Preferably it is less than 0.3 of a cell diameter and is preferably more than 0.1 cell diameters. Electrode needle 7 is provided with a plurality of sensing electrodes 15a, 15b, . . . 15n positioned near its proximal end 11. In this embodiment sensing electrodes 15a, 15b, . . . 15n are in the form of ring electrodes, preferably mounted flush with the surface of electrode needle 7 with the longitudinal axes of the ring electrodes concentric with the longitudinal axis of the electrode needle 7. Preferably the distances between the electrodes are chosen so that two or more electrodes can be inside the cell and one or more electrodes outside the cell being examined. In the case of an oocyte with a diameter of 1 mm, electrodes 15a-15n may each be 0.05-0.1 mm long in the longitudinal direction of the needle and spaced at 0.1-0.2 mm intervals. A further electrode 15(n+1) is provided on the exterior wall of electrode sheath 3.

The electrode needle 7 and electrode sheath 3 are either made of insulating material and/or insulating material is arranged on or in the electrode needle and electrode sheath in order to isolate the electrodes from each other. Optionally, electrode needle 7 can be provided with adjustable mounting means (not shown) for displacing electrode needle 7 up or down in its longitudinal direction. These adjustable mounting means may be used to move the free end of electrode needle 7 closer to or further away from the open end of electrode sheath 3 in order to vary the depth of penetration of the electrode needle into the cell that it is attached to. Each electrode 15a, 15b, . . . 15n+1 is connected by a conductor 17a, 17b, . . . 17n+1 to an input/output bus 19 of a computing and control device such as a personal computer 21. Computing and controlling device 21 is programmed to collect signals from electrodes 15a, 15b and to control an optional source of suction 23, such as a vacuum or suction pump or vacuum tank, connected via a suction line 25 to an opening 27 in well 35 which leads to the interior of electrode sheath 3. The source of suction 23 can be controlled to generate suction in electrode sheath 3 in order to hold cell 31 onto electrode needle 7. Alternatively, cell 31 may be retained on electrode needle 7 by a barb (not shown) or a lid (not shown) fitted over the top of well 35.

Single units or arrays of single units of cell holding electrode arrangements in accordance with the first to third embodiments of the present invention, or the like, could be arranged to penetrate and hold cells from above in order to perform a dipping procedure in a drug-free or drug-containing solution (e.g. a small quantity of drug may be contained in a micro-drop spotted out on a hydrophobic membrane, the cell may be dipped into the micro-drop, its response to the drug recorded and then it may be dipped in a drug free solution and its response recorded). Alternatively, units in accordance with the present invention could form arrays and operate with solution-containing wells, each containing a cell, with sides that guide the 'stinging' electrode(s) towards the cell.

Preferably, devices in accordance with the present invention are made integrally of moulded and/or machined plastic materials with subsequently attached metal electrodes.

While the present invention has been illustrated by examples of embodiments in which rigid needles carrying conducting portions pass through the cell membrane, it is also conceivable that a transmembranal hole may be introduced by a hollow needle-type mechanism or a lipolytic chemical treatment to form a non-selective ion conductance path (e.g. phospholipase doping, detergent doping). Extra conductor points in continuity with the intracellular solution could be used. Hollow, open-ended, electrolyte-containing needles, e.g. glass capillary needles containing conducting fluid are also conceivable.

The above mentioned embodiments are intended to illustrate the present invention and are not intended to limit the scope of protection claimed by the following claims.

What is claimed is:

1. A cell holding electrode arrangement comprising a hollow electrode sheath open at a cell-contact tip wherein said sheath surrounds at least one elongated electrode needle provided with a plurality of sensing electrodes, wherein at least one electrode is arranged at the proximity of the cell contact tip such that it, when a cell is held at the cell-contact tip, is arranged to penetrate the cell membrane of said cell, further wherein at least one other electrode is arranged at a distance from the cell contact tip such that it, when a cell is held at the cell-contact tip, is arranged to not penetrate the cell membrane of said cell, and wherein the open end of the hollow electrode sheath at the cell-contact tip has a diameter of between 0.1-0.8 mm.

2. The cell holding electrode arrangement of claim 1, wherein said needle does not extend beyond the cell-contact tip of said sheath.

3. The cell holding electrode arrangement of claim 1, wherein said needle is provided with a cell-removal preventing device.

4. The cell holding electrode arrangement of claim 1, wherein said needle is provided with a non-ion-conducting sealing compound.

5. The cell holding electrode arrangement of claim 1, wherein said sheath is arranged inside a well.

6. The cell holding electrode arrangement of claim 1, wherein said sheath is coupled to an automated manipulating device.

7. A method for positioning electrodes inside a cell comprising the steps of:
    positioning a cell at the cell contact tip of a cell holding electrode arrangement that includes a hollow electrode sheath open at a cell-contact tip wherein the sheath surrounds at least one elongated electrode needle provided with a plurality of sensing electrodes, wherein at least one electrode is arranged at the proximity of the cell contact tip and at least one other electrode at a distance from the cell contact tip, and wherein the open end of the hollow electrode sheath at the cell-contact tip has a diameter of between 0.1-0.8 mm; and
    penetrating the cell using the cell electrode holding arrangement such that said at least one electrode arranged at the proximity of the cell contact-tip penetrate the cell membrane of the cell, and such that said at least one other electrode arranged at a distance from the cell contact tip does not penetrate the cell membrane of said cell.

8. A method in accordance with claim 7 wherein positioning a cell further comprises pushing said cell onto the electrode needle.

9. The method of claim 7 wherein positioning a cell comprises applying a suction to the cell to pull the cell onto the electrode needle.

10. The method of claim 7 further comprising applying a suction to the cell based on a predetermined conductivity measurement.

11. The method of claim 7 further comprising:
    identifying a change in conductivity between the cell and the sensing electrode; and
    positioning the cell based on the change in conductivity.

12. A cell holding electrode arrangement comprising a hollow electrode sheath open at a cell-contact tip wherein said sheath surrounds a plurality of elongated electrode needles each provided with at least one sensing electrode, wherein at least one electrode needle is arranged at the proximity of the cell contact tip such that it, when a cell is held at the cell-contact tip, is arranged to penetrate the cell membrane of said cell, wherein at least one other electrode needle is arranged at a distance from the cell contact tip such that it, when a cell is held at the cell-contact tip, is arranged to not penetrate the cell membrane of said cell, and wherein the open end of the hollow electrode sheath at the cell-contact tip has a diameter of between 0.1-0.8 mm.

13. The cell holding electrode arrangement of claim 12 wherein at least one of said needles comprises a barbed device to retain the cell on said needle.

14. The cell holding electrode arrangement of claim 12 wherein at least one of said needles comprises a tapered ring to retain said cell on said needle.

15. The cell holding electrode arrangement of claim 12 further comprising a vacuum pump, said vacuum pump creating a vacuum within said sheath based on a measured conductivity.

16. The cell holding electrode arrangement of claim 12 further comprising a reference electrode, said cell holding arrangement configured to create a vacuum in said sheath based on a conductivity change measured between the reference electrode and said sensing electrode.

17. The cell holding electrode arrangement of claim 12 further comprising a strengthening tube positioned in said sheath and surrounding said plurality of electrode needles, said strengthening tube configured to prevent buckling of said electrode needles.

* * * * *